(12) United States Patent
Ozawa

(10) Patent No.: US 6,638,624 B2
(45) Date of Patent: Oct. 28, 2003

(54) SQUARYLIUM DYE AND FILTER FOR DISPLAY DEVICE

(75) Inventor: Tetsuo Ozawa, Kanagawa (JP)

(73) Assignee: Mitsubishi Chemical Corporation, Tokyo (JP)

(*) Notice: Subject to any disclaimer, the term of this patent is extended or adjusted under 35 U.S.C. 154(b) by 94 days.

(21) Appl. No.: 09/861,714

(22) Filed: May 22, 2001

(65) Prior Publication Data

US 2002/0012182 A1 Jan. 31, 2002

(30) Foreign Application Priority Data

May 22, 2000 (JP) ........................................ 2000-149260
Jul. 19, 2000 (JP) ........................................ 2000-218194

(51) Int. Cl.$^7$ ........................ C07D 403/02; G02B 5/22; H01J 17/49
(52) U.S. Cl. ........................ 428/411.1; 106/31.49; 106/31.78; 548/365.1; 359/885; 313/112; 313/582
(58) Field of Search ............ 428/411.1; 106/31.49, 106/31.78; 548/365.1; 359/885, 893; 313/112, 582

(56) References Cited

U.S. PATENT DOCUMENTS

| 4,175,956 A | 11/1979 | Haley et al. ............... 430/37 |
| 4,353,971 A | * 10/1982 | Chang et al. ............... 252/500 |
| 6,157,504 A | * 12/2000 | Yamada et al. ............. 252/582 |

FOREIGN PATENT DOCUMENTS

| JP | 61-188501 | 8/1986 |
| JP | 10-26704 | 1/1998 |
| JP | 2000-43175 | 2/2000 |
| JP | 2000-193820 | 7/2000 |
| JP | 2000-345059 | 12/2000 |
| WO | WO 98/23980 | 6/1998 |
| WO | WO 98/57201 | 12/1998 |
| WO | WO 99/01883 | 1/1999 |

OTHER PUBLICATIONS

H.-E. Sprenger, et al., Angew. Chem. Internat. Edit., vol. 7, No. 7, pp. 530–535, "Cyclobutenediylium Dyes", Jul. 1968.

* cited by examiner

Primary Examiner—Ramsey Zacharia
(74) Attorney, Agent, or Firm—Oblon, Spivak, McClelland, Maier & Neustadt, P.C.

(57) ABSTRACT

A filter for a display device, which comprises a dipyrazolylsquarylium dye represented by formula:

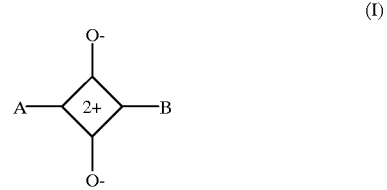

(I)

wherein A and B each independently represent a substituted or unsubstituted pyrazolyl group. The filter is excellent in resistance to heat and light and gives no adverse influences on luminescence of the three primary colors, red, green and blue.

15 Claims, 2 Drawing Sheets

SQUARYLIUM DYE AND FILTER FOR DISPLAY DEVICE

FIELD OF THE INVENTION

This invention relates to coloring matter for a filter for electronic display devices and a filter containing the coloring matter for display panels. More particularly, the invention relates to a specific squarylium dye and a display filter containing the same which is capable of controlling the tone of an electronic display device or increasing the purity of luminescence color without reducing the luminescence intensity of the display device.

BACKGROUND OF THE INVENTION

Color display devices hitherto developed include CRTs, vacuum fluorescent tubes, field-emission displays, plasma display panels (PDPs), liquid crystal displays, and electroluminescence displays. In these display devices, an image is displayed by combinations of luminescence of three primary colors, red, green and blue. In order to obtain a clear color image with corrected color balance, it is necessary to use a so-called band pass filter which can absorb unnecessary luminescence other than the three primary colors. Various band pass filters containing coloring matter have been studied for this use. It is important for the coloring matter used in the band pass filters to have no absorptions other than a desired absorption and to have sufficient resistance to heat and light.

Known color correction filters for displays include those containing commercially available coloring matter which selectively absorbs light of specific wavelengths, as disclosed, e.g., in JP-A-61-188501, JP-A-10-26704, WO98/57201, WO98/23980, and WO99/1983. The problem of these conventional color correction methods lies in that the filter absorbs part of necessary components of the three primary colors only to impair the color balance or to darken the display.

An antireflective film containing a squarylium compound has recently been proposed as disclosed, e.g., in JP-A-2000-43175. However, the disclosure does not refer to a dipyrazolylsquarylium compound as a specific example of the squarylium compound nor the correlation between the compound structure and a light transmission at various wavelengths.

With reference to pyrazolylsquarylium compounds, Angew. Chem. Internat. Edit., vol. 7, p. 530 (1968) describes that an N-phenyl dipyrazolylsquarylium compound is an orange color but has no mention of the absorption spectral wave form, etc. of the compound.

U.S. Pat. No. 4,175,956 discloses an N-phenyl dipyrazolylsquarylium compound as a red color useful as an electrophotographic photoreceptor without referring to the transmissions at various wavelengths.

SUMMARY OF THE INVENTION

An object of the present invention is to provide coloring matter for display filters, which has a transmission spectrum having a sharp minimum value in a wavelength region of from 480 to 520 nm and which is therefore capable of selectively cutting light of wavelengths t the valley between blue and green.

Another object of the present invention is to provide a display filter, such as a color correction filter, a color purity improving filter, and a color reproduction range broadening filter, which performs the desired function without adversely affecting luminescence of the three primary colors, red, blue and green.

As a result of extensive investigation, the present inventors have found that the above objects of the invention are accomplished by a specific squarylium dye having a pyrazolyl group.

The present invention provides:

coloring matter for a filter of a display device which comprises a dipyrazolylsquarylium compound represented by formula (I):

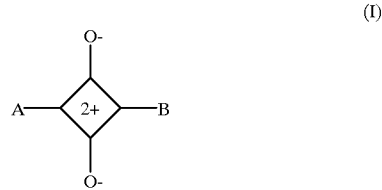

wherein A and B each independently represent a substituted or unsubstituted pyrazolyl group;

a display filter containing the coloring matter; and a squarylium compound represented by formula (II):

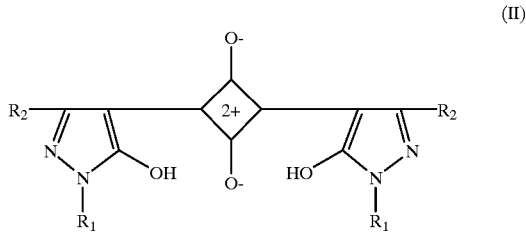

wherein $R_1$ represents a substituted or unsubstituted alkyl group; $R_2$ represents a substituted or unsubstituted alkyl group or a substituted or unsubstituted aryl group; and $R_1$ and $R_2$ may be the same or different.

The filter according to the present invention exhibit s excellent durability, such as heat resistance and light resistance, and gives no adverse influences on luminescence of the three primary colors.

DETAILED DESCRIPTION OF THE INVENTION

Figure 1:
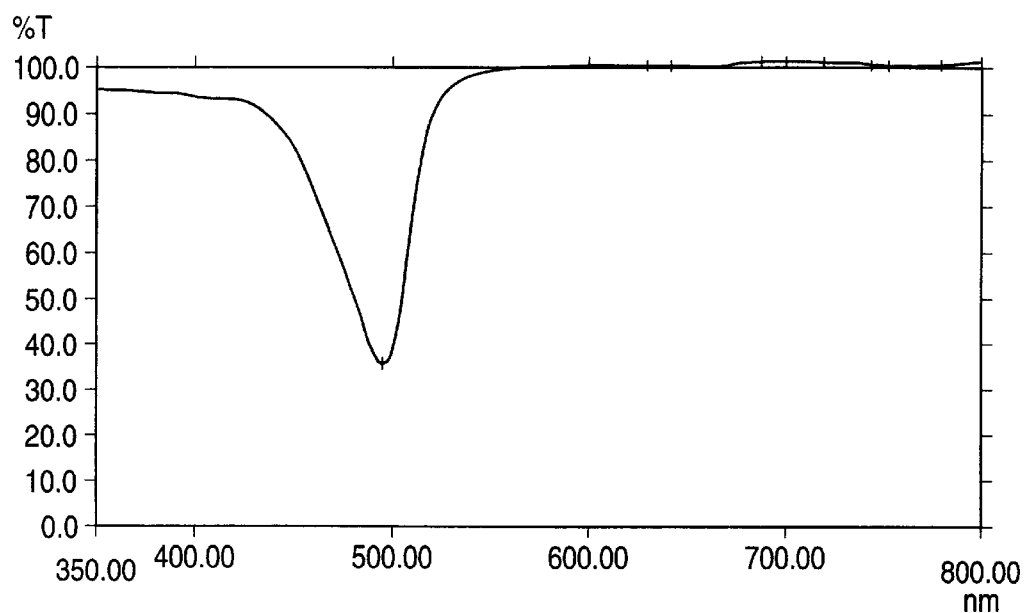
FIG. 1 is a transmission spectrum of the coating film obtained in Example 5.

The coloring matter for display filters according to the invention comprises a dipyrazolylsquarylium compound represented by formula (I) which is orange to red coloring matter. The dipyrazolylsquarylium compound of formula (I) is characterized by a pyrazole ring disposed on both ends of the molecule.

In formula (I), the pyrazolyl groups as represented by A and B may each independently have an arbitrary substituent (s) as long as the compound has a minimum transmission in a wavelength region of from 480 to 520 nm. The substituted pyrazolyl group usually has a molecular weight of 500 or less. The pyrazolyl groups are preferably substituted or unsubstituted 4-pyrazolyl groups, still preferably those represented by formula (IV):

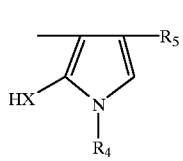
(IV)

wherein $R_4$ represents a substituted or unsubstituted alkyl group or a substituted or unsubstituted aryl group; $R_5$ represents a substituted or unsubstituted alkyl group, a substituted or unsubstituted alkoxy group, a substituted or unsubstituted aryl group, a substituted or unsubstituted amino group, a substituted or unsubstituted alkoxycarbonyl group or a substituted or unsubstituted aryloxycarbonyl group; and X represents an oxygen atom or an NH group.

In formula (IV), $R_4$ represents a substituted or unsubstituted alkyl group or a substituted or unsubstituted aryl group, and $R_4$ preferably represents a substituted or unsubstituted alkyl group.

The alkyl group of $R_4$ includes straight-chain, branched or cyclic alkyl groups having 1 to 20 carbon atoms, such as methyl, ethyl, propyl, butyl, pentyl, hexyl, heptyl, octyl, decyl, undecyl, dodecyl, tridecyl, pentadecyl, and cyclohexyl. The aryl group of $R_4$ includes phenyl and naphthyl.

The substituents of the alkyl group or the aryl group include an alkyl group having 1 to 10 carbon atoms, e.g., methyl, ethyl, propyl, butyl, pentyl, hexyl, heptyl, octyl or decyl; an alkoxy group having 1 to 10 carbon atoms, e.g., methoxy, ethoxy, propoxy, butoxy, pentyloxy, hexyloxy, heptyloxy, octyloxy or decyloxy; an aryl group, e.g., phenyl or naphthyl; an aryloxy group, e.g., phenoxy or naphthyloxy; a sulfonylamido group which may be substituted with an alkyl or aryl group, e.g., sulfonylamido, alkylsulfonylamido, dialkylsulfonylamido, arylsulfonylamido, diarylsulfonylamido or alkylarylsulfonylamido; a nitro group; a hydroxyl group; and a halogen atom, e.g., fluorine, chlorine or bromine.

Preferred examples of the substituted or unsubstituted alkyl group as $R_4$ are straight-chain or branched alkyl groups having 1 to 20 carbon atoms which may have a substituent(s) selected from an alkoxy group, an aryl group, an aryloxy group, a hydroxyl group, and a halogen atom, particularly those which may be substituted with an alkoxy group or a halogen atom, especially unsubstituted alkyl groups having 1 to 8 carbon atoms.

Preferred examples of the substituted or unsubstituted aryl group as $R_4$ include those which may be substituted with an alkyl group, an alkoxy group, a sulfonylamido group, a hydroxyl group or a halogen atom, particularly those which may be substituted with an alkyl group, an alkoxy group or a halogen atom, with a phenyl group or an alkylphenyl group being especially preferred.

In formula (IV), $R_5$ represents a substituted or unsubstituted alkyl group, a substituted or unsubstituted alkoxy group, a substituted or unsubstituted aryl group, a substituted or unsubstituted amino group, a substituted or unsubstituted alkoxycarbonyl group or a substituted or unsubstituted aryloxycarbonyl group, and $R^5$ preferably represents a substituted or unsubstituted alkyl group or a substituted or unsubstituted aryl group, with a substituted or unsubstituted alkyl group being particularly preferred.

Examples of the substituted or unsubstituted alkyl group of $R_5$ are the same as those enumerated as for $R_4$.

The alkoxy group of $R_5$ includes those having 1 to 20 carbon atoms, such as methoxy, ethoxy, propoxy, butoxy, pentyloxy, hexyloxy, heptyloxy, octyloxy, and decyloxy. The substituents of the substituted alkoxy group include an alkyl group having 1 to 10 carbon atoms, e.g., methyl, ethyl, propyl, butyl, pentyl, hexyl, heptyl, octyl, and decyl; an alkoxy group having 1 to 10 carbon atoms, such as methoxy, ethoxy, propoxy, butoxy, pentyloxy, hexyloxy, heptyloxy, octyloxy, and decyloxy; an aryl group, such as phenyl or naphthyl; an aryloxy group, e.g., phenoxy or naphthyloxy; a hydroxyl group, and a halogen atom, e.g., fluorine, chlorine or bromine.

Examples of the substituted or unsubstituted aryl group as $R_5$ are the same as those recited for $R_4$.

Examples of the substituted or unsubstituted amino group as $R_5$ include an unsubstituted amino group; an amino group substituted with a straight-chain or branched alkyl group having 1 to 20 carbon atoms, e.g., methyl, ethyl, propyl, butyl, pentyl, hexyl, heptyl, octyl, decyl, undecyl, dodecyl, tridecyl or pentadecyl; and an amino group substituted with an acyl group, e.g., acetyl, propionyl or butyryl.

The alkoxycarbonyl group of $R_5$ includes straight-chain or branched alkoxycarbonyl group having 1 to 20 carbon atoms, such as methoxycarbonyl, ethoxycarbonyl, propoxycarbonyl, butoxycarbonyl, pentyloxycarbonyl, hexyloxycarbonyl, heptyloxycarbonyl, and octyloxycarbonyl. Examples of the substituents of the substituted alkoxycarbonyl group are the same as those described above for the substituted alkoxy group.

The substituted or unsubstituted aryloxycarbonyl group as $R_5$ includes an aryloxycarbonyl group which may be substituted with an alkyl or alkoxy group, such as phenyloxycarbonyl, p-tolyloxycarbonyl and p-methoxyphenyloxycarbonyl.

X in the formula (I) represents an oxygen atom or NH, preferably an oxygen atom.

While A and B in formula (I) may be either the same or different, it is preferred for the compound of formula (I) be symmetrical (A=B) for stability as a dye and ease of synthesis.

Specific examples of the compounds of formula (I) are shown in Table 1 below.

TABLE 1

(I)

[Structure: squarate dianion with A and B substituents, 2+ charge on ring, two O⁻ groups]

A = B = [pyrazole structure with R5, N-R4, and HX substituents]

| NO. | —A —R4 | —R5 | X | —B —R4 | —R5 | X |
|---|---|---|---|---|---|---|
| 1 | —CH3 | —CH3 | O | —CH3 | —CH3 | O |
| 2 | —CH3 | —C2H5 | O | —CH3 | —C2H5 | O |
| 3 | —CH3 | —C3H7(n) | O | —CH3 | —C3H7(n) | O |
| 4 | —CH3 | —C4H9(n) | O | —CH3 | —C4H9(n) | O |
| 5 | —CH3 | —C4H9(t) | O | —CH3 | —C4H9(t) | O |
| 6 | —C2H5 | —C6H13(n) | O | —C2H5 | —C6H13(n) | O |
| 7 | —C4H9(n) | —CH3 | O | —C4H9(n) | —CH3 | O |
| 8 | —C3H7(n) | —C4H9(t) | O | —C3H7(n) | —C4H9(t) | O |
| 9 | —CH3 | —COOC2H5 | O | —CH3 | —COOC2H5 | O |
| 10 | —C4H9(t) | —COOC6H5 | O | —C4H9(t) | —COOC6H5 | O |
| 11 | —C6H4—CH3 (p-tolyl) | —CH3 | O | —C6H4—CH3 (p-tolyl) | —CH3 | O |
| 12 | —C6H5 (phenyl) | —C4H9(t) | O | —C6H5 (phenyl) | —C4H9(t) | O |
| 13 | —C6H5 (phenyl) | —CH3 | NH | —C6H5 (phenyl) | —CH3 | NH |
| 14 | —C6H5 (phenyl) | —NH2 | O | —C6H5 (phenyl) | —NH2 | O |
| 15 | —CH3 | —OC2H5 | O | —CH3 | —OC2H5 | O |
| 16 | —C4H9(t) | —C6H5 (phenyl) | O | —C4H9(t) | —C6H5 (phenyl) | O |
| 17 | —CH3 | —C6H5 (phenyl) | O | —CH3 | —C6H5 (phenyl) | O |

Of the preferred compounds of formula (I) in which substituents A and B are selected from the above-described preferred substituted pyrazolyl groups, still preferred are those represented by formula (II):

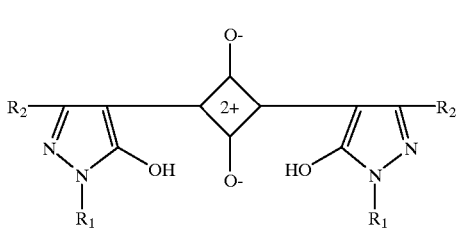

(II)

wherein $R_1$ represents a substituted or unsubstituted alkyl group; $R_2$ represents a substituted or unsubstituted alkyl group or a substituted or unsubstituted aryl group; and $R_1$ and $R_2$ may be the same or different.

Among the compounds of formula (II), particularly preferred are those in which $R_2$ is a substituted or unsubstituted alkyl group.

The dipyrazolylsquarylium compounds of formula (II) are novel compounds which effectively and selectively absorb light in the region 480 to 520 nm between a blue color and a green color with a particularly narrow half-value width so that they do not hinder primary blue or green fluorescence. Therefore, they are particularly useful dyes for color correction, improving color purity or broadening the color reproduction range.

The substituted or unsubstituted alkyl group and the substituted or unsubstituted aryl group as $R_1$ or $R_2$ include those enumerated for $R_4$ and $R_5$.

$R_1$ is preferably an alkyl group which may be substituted with an alkoxy group or a halogen atom, still preferably an unsubstituted alkyl group having 1 to 8 carbon atoms.

$R_2$ is preferably an alkyl group which may be substituted with an alkoxy group or a halogen atom or an aryl group which may be substituted with an alkyl group, an alkoxy group or a halogen atom, still preferably an unsubstituted alkyl group having 1 to 8 carbon atoms, a phenyl group or an alkylphenyl group, particularly preferably an unsubstituted alkyl group having 1 to 8 carbon atoms.

The dipyrazolylsquarylium compounds represented by formula (I) or (II) are synthesized by, for example, dehydrating condensation between 1 mol of squarylic acid and 2 mol of a pyrazolone compound represented by formula (V) or (VI):

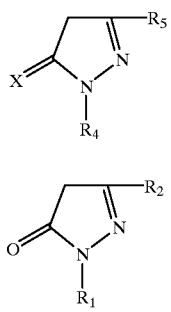

(V)

(VI)

wherein $R_1$, $R_2$, $R_4$, $R_5$, and X are as defined above, in a solvent (e.g., ethanol, acetic acid, an n-butyl alcohol/toluene mixed solvent or an n-butyl alcohol/benzene mixed solvent) at about 70 to 150° C. by utilizing the process disclosed in *Angew. Chem.*, vol. 77, pp. 680–681 (1965) or an appropriate combination of other known processes.

The filter for a display according to the invention contains at least one dye selected from the dipyrazolylsquarylium compounds of formula (I). Representative examples of the configuration of the filter includes a laminate structure composed of a transparent sheet or film substrate and a resin layer containing the dipyrazolylsquarylium compound and a binder resin, and a single layer structure, i.e., a sheet or film made of a resin containing the dipyrazolylsquarylium compound.

In using two or more dipyrazolylsquarylium compounds, they can be mixed up into a single layer of the above laminate or a single film above, or a plurality of layers or films each containing a dipyrazolylsquarylium compound may be provided. In such a case, a laminated is formed even in the above-described latter case. Moreover, by changing the binder resins depending on the respective dipyrazolylsquarylium compounds used, a subtle toning can be obtained.

The former laminate filter can be prepared by, for example, (1) a method comprising dissolving or dispersing the dipyrazolylsquarylium compound and a binder resin in an appropriate solvent and applying the solution or dispersion on a transparent sheet or film substrate by a conventional method, followed by drying, (2) a method comprising melt-kneading the dipyrazolylsquarylium compound and a binder resin, molding the mixture into a film or a sheet by a conventional molding technique for thermoplastic resins such as extrusion, injection molding or compression molding, and adhering the film or sheet to a transparent substrate, e.g., with an adhesive, (3) a method comprising extrusion laminating a molten mixture of the dipyrazolylsquarylium compound and a binder resin on a transparent substrate, (4) a method comprising co-extruding a molten mixture of the dipyrazolylsquarylium compound and a binder resin with a molten resin for a transparent substrate, or (5) a method comprising molding a binder resin into a film or a sheet by extrusion, injection molding, compression molding, etc., bringing the film or the sheet into contact with a solution of the dipyrazolylsquarylium compound, and the thus dyed film or sheet is adhered to a transparent substrate, e.g., with an adhesive.

The latter single layer sheet or film comprising a resin containing the dipyrazolylsquarylium compound is prepared by, for example, (6) a method comprising casting a solution or dispersion of the dipyrazolylsquarylium compound and a binder resin in an appropriate solvent on a carrier followed by drying, (7) a method comprising melt-kneading the dipyrazolylsquarylium compound and a binder resin and molding the mixture into a film or a sheet by a conventional molding technique for thermoplastic resins such as extrusion, injection molding or compression molding, or (8) a method comprising molding a binder resin into a film or a sheet by extrusion, injection molding, compression molding, etc. and bringing the film or the sheet into contact with a solution of the dipyrazolylsquarylium compound.

The laminate filter is preferred to the single layer filter. The laminate filter is preferably a laminated filter comprising a transparent substrate formed thereon a dipyrazolylsquarylium compound-containing resin layer comprising a binder resin containing the dipyrazolylsquarylium compound, which is produced by coating a transparent sheet or film substrate with a coating composition prepared by dissolving the dipyrazolylsquarylium compound and a binder resin in an appropriate solvent or dispersing the particles of the dipyrazolylsquarylium compound having a particle size of 0.1 to 3 μm and a binder resin in a solvent and drying the coating film.

The method of making the filter is chosen according to the layer structure and material fit for a particular use. Taking for instance a filter for plasma display panels (PDPs), which is an especially preferred embodiment of the present invention, the following production method is preferred.

Materials of the transparent substrate which can be used in the filter for PDPs are not particularly limited as far as they are substantially transparent, having little light absorption and causing little light scattering. Examples of suitable materials include glass, polyolefin resins, amorphous polyolefin resins, polyester resins, polycarbonate resins, acrylic resins, polystyrene resins, polyvinyl chloride resins, polyvinyl acetate resins, polyarylate resins, and polyether sulfone resins. Preferred of them are amorphous polyolefin resins, polyester resins, polycarbonate resins, acrylic resins, polyarylate resins, and polyether sulfone resins.

The resin is molded into a film or a sheet by conventional molding methods, such as injection molding, T-die extrusion, calendering and compression molding, or by casting a solution of the resin in an organic solvent. The resin can contain commonly known additives, such as anti-heat aging agents, lubricants, and antioxidants. The substrate usually has a thickness of 10 μm to 5 mm. The resin film or sheet may be unstretched or stretched film or sheet. The substrate may be a laminate of the above-described material and other films or sheets.

If desired, the transparent substrate can be subjected to a known surface treatment, such as a corona discharge treatment, a flame treatment, a plasma treatment, a glow discharge treatment, a surface roughening treatment, and a chemical treatment. If desired, the substrate can be coated with an anchoring agent or a primer.

The binder resin which can be used with the dipyrazolylsquarylium compound includes acrylic resins, polycarbonate resins, ethylene-vinyl alcohol copolymer resins, ethylene-vinyl acetate copolymer resins and saponification products thereof, AS resins, polyester resins, vinyl chloride-vinyl acetate copolymer resins, polyvinyl butyral resins, polyvinylphosphonic acid (PVPA), polystyrene resins, phenolic resins, phenoxy resins, polysulfone, nylon, cellulosic resins, and cellulose acetate resins. Preferred of them are polyester resins and acrylic resins.

The solvent which can be used for dissolving or dispersing the dye and the resin includes alkanes, such as butane, pentane, hexane, heptane, and octane; cycloalkanes, such as cyclopentane, cyclohexane, cycloheptane, and cyclooctane; alcohols, such as ethanol, propanol, butanol, amyl alcohol, hexanol, heptanol, octanol, decanol, undecanol, diacetone alcohol, and furfuryl alcohol; cellosolves, such as methyl cellosolve, ethyl cellosolve, butyl cellosolve, methyl cellosolve acetate, and ethyl cellosolve acetate; propylene glycol and its derivatives, such as propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate, and dipropylene glycol dimethyl ether; ketones, such as acetone, methyl amyl ketone, cyclohexanone, and acetophenone; ethers, such as dioxane and tetrahydrofuran; esters, such as butyl acetate, amyl acetate, ethyl butyrate, butyl butyrate, diethyl oxalate, ethyl pyruvate, ethyl 2-hydroxybutyrate, ethyl acetoacetate, methyl lactate, ethyl lactate, and methyl 3-methoxypropionate; halogenated hydrocarbons, such as chloroform, methylene chloride, and tetrachloroethane; aromatic hydrocarbons, such as benzene, toluene, xylene, and cresol; and highly polar solvents, such as dimethyl formamide, dimethyl acetamide, and N-methylpyrrolidone.

The solution or dispersion of the dipyrazolylsquarylium compound and the binder resin can contain a dispersant, such as a polyvinyl butyral resin, a phenoxy resin, a phenolic resin (e.g., a rosin-modified phenol resin), a petroleum resin, a rosin resin (e.g., hardened rosin, a rosin ester, and maleic acid-modified rosin), and a polyurethane resin. The dispersant is usually used in an amount of about 0.01 to 10 parts by weight per 100 parts by weight of the dipyrazolylsquarylium compound.

The total concentration of the dipyrazolylsquarylium compound, the binder, the dispersant, etc. in the resin solution or dispersion is 0.5 to 50% by weight. The proportion of the dipyrazolylsquarylium compound in the solute or dispersoid is 0.05 to 50% by weight, preferably 0.1 to 20% by weight.

The solution or dispersion containing the dipyrazolylsquarylium compound is applied to the transparent substrate by known coating techniques, such as dip coating, flow coating, spray coating, bar coating, gravure coating, roll coating, blade coating, and air knife coating. The solution or dispersion is usually applied to a dry coating thickness of 0.1 to 30 μm, preferably 0.5 to 10 μm.

It is preferred that the display filter containing the dipyrazolylsquarylium compound have a transmission spectrum which depicts a sharp valley with its minimum value being in a wavelength region of from 480 to 520 nm so as not to interfere with blue and/or green fluorescence. The half-value width of the valley is preferably 60 nm or less. In order not to reduce brightness of a display, it is preferred for the filter to have no minimum values other than the above-specified one in its transmission spectrum. In order not to interfere with blue and/or green fluorescence, the transmissions of the filter at 450 nm, 500 nm, and 550 nm are preferably 70% or more, 20% or more, and 70% or more, respectively.

For use as a band pass filter for a PDP, it is preferred for the filter to contain a diphenylsquarylium compound represented by formula (III) shown below in addition to the dipyrazolylsquarylium compound to further improve the color balance.

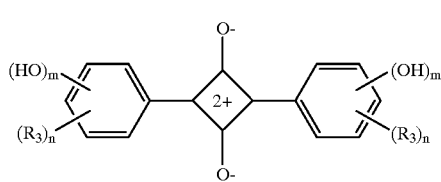

(III)

wherein $R_3$ represents a halogen atom, a substituted or unsubstituted alkyl group, a substituted or unsubstituted alkoxy group or a substituted or unsubstituted alkenyl group; m represents an integer of 1 to 4; and n represents an integer of 0 to 4.

Preferred examples of $R_3$ include:
(i) a halogen atom, such as fluorine, chlorine or bromine;
(ii) a straight-chain or branched alkyl group having 1 to 20 carbon atoms, such as methyl, ethyl, propyl, butyl, pentyl, hexyl, heptyl, octyl, decyl, undecyl, dodecyl, tridecyl or pentadecyl;
(iii) a straight-chain or branched alkyl group having 1 to 20 carbon atoms, which is substituted with a hydroxyl group, an alkoxycarbonyl group (e.g., methoxycarbonyl, ethoxycarbonyl or butoxycarbonyl), an acyloxycarbonyl group (e.g., acetyloxycarbonyl or propionyloxycarbonyl), an alkoxycarbonyloxy group (e.g., methoxycarbonyloxy, ethoxycarbonyloxy or butoxycarbonyloxy), etc.;

(iv) a straight-chain or branched alkoxy group having 1 to 20 carbon atoms, such as methoxy, ethoxy, propoxy, butoxy, pentyloxy, hexyloxy, heptyloxy, octyloxy, decyloxy, undecyloxy, dodecyloxy, tridecyloxy or pentadecyloxy;

(v) a straight-chain or branched alkoxy group having 1 to 20 carbon atoms, which is substituted with an alkoxy group having 1 to 8 carbon atoms, such as methoxy, ethoxy, propoxy, butoxy, pentyloxy, hexyloxy, heptyloxy or octyloxy;

(vi) an alkenyl group, such as an ethenyl group; and (vii) an alkenyl group (e.g., ethenyl) substituted with an alkyl group (e.g., methyl, ethyl, propyl, butyl, pentyl, hexyl, heptyl, octyl or decyl), a phenyl group, a 4-hydroxyphenyl group, a 4-alkoxy(e.g., $C_1$–$C_{10}$ alkoxy)phenyl group, a 3,4-bisalkoxy(e.g., $C_1$–$C_{10}$ alkoxy)phenyl group, a 3,5-bisalkoxy(e.g., $C_1$–$C_{10}$ alkoxy)phenyl group or a 3,4,5-trisalkoxy(e.g., $C_1$–$C_{10}$ alkoxy)phenyl group.

$R_3$ is preferably a straight-chain or branched alkyl group having 1 to 6 carbon atoms which may be substituted with a hydroxyl group or an alkoxycarbonyl group, an alkoxy group having 1 to 6 carbon atoms or a substituted ethenyl group, with an alkyl group having 1 to 6 carbon atoms being particularly preferred.

Among the compounds of formula (III) those in which m is 3 are preferred, because they have no minimum value and no absorption in a range of about 400 to 500 nm and having a satisfactory transmission in that range. Of the compounds of formula (III), those having a symmetric molecular structure are preferred for ease of synthesis. Examples of preferred chemical structures of formula (III) are shown below.

III-1

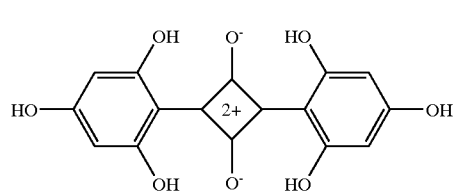

III-2

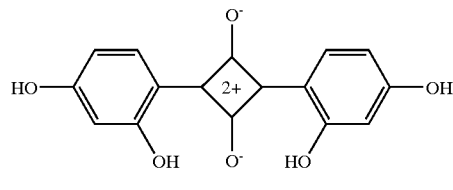

III-3

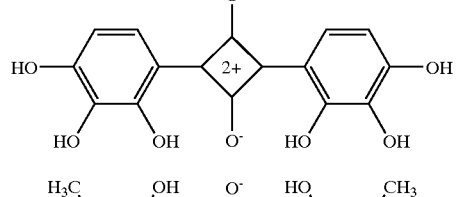

III-4

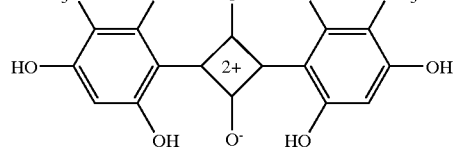

-continued

III-5

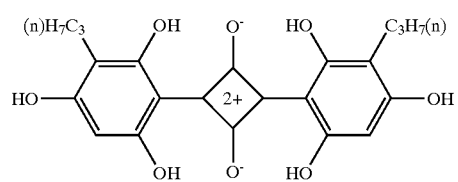

III-6

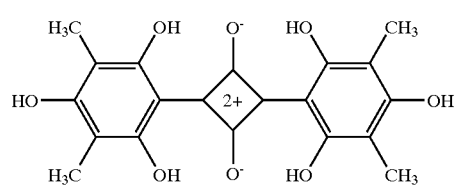

III-7

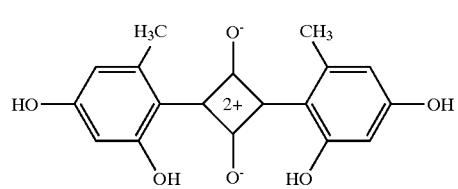

III-8

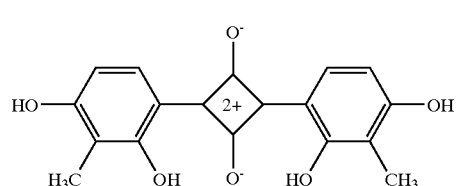

III-9

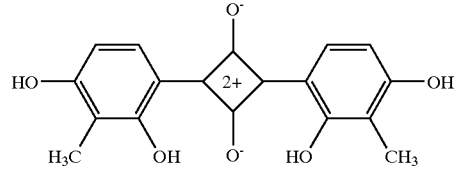

III-10

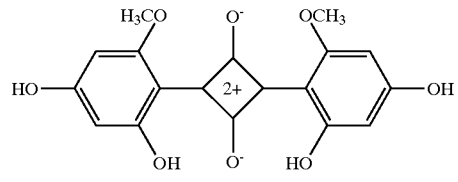

III-11

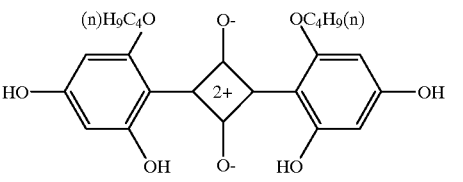

III-12

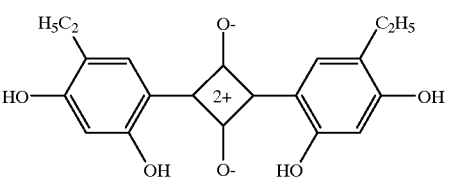

The diphenylsquarylium compound of formula (III) is a blue dye and preferably cuts neon luminescence at around 590 nm but does not cut green luminescence at around 530 nm and red luminescence of 600 nm or longer wavelengths that are luminescent colors of phosphors. In other words, it is preferred for the diphenylsquarylium compound to have a transmission spectrum depicting a sharp valley with a minimum value within a wavelength range of from 570 to 605 nm, particularly 580 to 600 nm, in which the minimum transmission in that range is preferably 30% or less, still preferably 25% or less, with a half-value width of the valley being preferably 60 nm or less.

In addition, the transmission spectrum preferably shows a sharp rise from the valley in the longer wavelength side. Specifically, the ratio of the part of the valley area between the wavelength of the minimum value and 650 nm to the total valley area between 550 nm and 650 nm is preferably 50% or less, still preferably 48% or less, particularly preferably 45% or less.

In order to secure the brightness of a plasma display, it is preferred for the transmission spectrum of the diphenylsquarylium compound not to have a minimum value in a wavelength region of from 550 to 650 nm except the above-specified minimum value at about 590 nm. If the spectrum has any minimum other than the one at about 590 nm, the transmission of the former should be at least 70%, preferably at least 80%.

The diphenylsquarylium compounds represented by formula (III) are synthesized by, for example, dehydrating condensation between 2 mol of a substituted phenol compound corresponding to the substituted phenyl group of formula (III) and 1 mol of squarylic acid (3,4-dihydroxy-3-cyclobutene-1,2-dione) in a solvent (e.g., ethanol, acetic acid, an n-butyl alcohol/toluene mixed solvent or an n-butyl alcohol/benzene mixed solvent) at about 70 to 150° C. in accordance with the process disclosed in *Angew. Chem.*, vol. 77, pp. 680–681 (1965) or a combination of other known processes.

The diphenylsquarylium compound of formula (III) is used in an amount usually of from 0.01 to 50% by weight, preferably of from 0.05 to 20% by weight, based on the sum of the diphenylsquarylium compound, the dipyrazolylsquarylium compound of formula (I) or (II), the binder, and the dispersant. The weight ratio of the diphenylsquarylium compound to the dipyrazolylsquarylium compound is about 0.6 to 10. In general, the filter tends to assume a green tint when the amount of dipyrazolylsquarylium compound is too low, and it tends to assume a red tint when it is too high.

The display filter containing both the dipyrazolylsquarylium compound of formula (I) or (II) and the diphenylsquarylium compound of formula (III) preferably has a visible light transmission of 50% or more, particularly 60% or more.

For the addition of the diphenylsquarylium compound to the display filter, the diphenylsquarylium compound and the dipyrazolylsquarylium compound can be used as a mixture together with the binder resin, or they can be separately mixed with the respective binder resins to form separate layers in a filter.

The filter having a laminate structure comprising the transparent sheet film substrate having formed thereon the dipyrazolylsquarylium compound-containing resin layer which can further contain the diphenylsquarylium compound or the dipyrazolylsquarylium compound-containing resin layer and a diphenylsquarylium compound-containing resin layer or the filter made of the dipyrazolylsquarylium compound-containing resin layer can further contain other coloring matter capable of absorbing visible light, such as yellow light, red light or blue light, in the dipyrazolylsquarylium compound- and/or the diphenylsquarylium compound-containing resin layer or an independent layer. Such coloring matter includes an anthraquinone type, an azo type, a phthalocyanine type, a pyrromethene type, a cyanine type, a squarylium type except those referred to above, and a methine type.

It is preferred for the display filter to contain an antioxidant or an ultraviolet (UV) absorber. An antioxidant is preferably incorporated into the dipyrazolylsquarylium compound-containing resin layer. A UV absorber is preferably incorporated into a layer independent of the dipyrazolylsquarylium compound-containing layer though it is possible to incorporate it into the dipyrazolylsquarylium compound-containing layer. For example, a UV absorber is mixed with a binder resin, such as those recited above, and applied to a dry thickness of 0.1 to 30 μm, preferably 0.5 to 10 μm, or a UV absorber can be incorporated into the aforementioned transparent substrate.

In a highly preferred embodiment, a UV absorber-containing layer is provided independently of the dipyrazolylsquarylium compound-containing resin layer in outer side position than the dipyrazolylsquarylium compound-containing resin layer (in a position opposite to the side at which the display divide is adhered).

Antioxidants which can be used in the invention include phenolic compounds such as 2,6-di-t-butyl-p-cresol, 2,6-di-t-butyl-4-hydroxymethylphenol, 2,6-di-t-butyl-4-ethylphenol, 2,4,6-tri-t-butylphenol, n-octadecyl 3-(3',5'-di-t-butyl-4'-hydroxyphenyl)propionate, stearyl β-(3,5-di-t-butyl-4-hydroxyphenyl)propionate, 2,2'-methylenebis(4-methyl-6-t-butylphenol), 2,2'-methylenebis(4-ethyl-6-t-butylphenol), 4,4'-isopropylidenebisphenol, 4,4'-methylenebis(2,6-di-t-butylphenol), 4,4'-butylidenebis(3-methyl-6-t-butylphenol), 1,1-bis(4'-hydroxyphenyl)cyclohexane, 2,6-bis(2'-hydroxy-3'-t-butyl -5'-methylbenzyl)-4-methylphenol, 2,2'-thiobis(4-methyl-6-t-butylphenol), 4,4'-thiobis(2-methyl-6-t-butylphenol), 4,4'-thiobis(3-methyl-6-t-butylphenol), 1,1,3-tris(2'-methyl-4'-hydroxy-5'-t-butylphenyl)butane, 1,3,5-trimethyl-2,4,6-tris(3',5'-di-t-butyl-41-hydroxybenzyl)benzene, tris(3,5-di-t-butyl-4-hydroxyphenyl)isocyanurate, tris [(β-(3,5-di-t-butyl-4-hydroxyphenyl)propionyloxyethyl]isocyanurate, and tetrakis[methylene-3-(3',5'-di-t-butyl-4'-hydroxyphenyl)propionate]methane; sulfur-containing compounds, such as dilauryl thiodipropionate, dimyristyl thiodipropionate, and distearyl thiodipropionate; and phosphorus-containing compounds, such as triphenyl phosphite, diphenylisodecyl phosphite, phenyldiisodecyl phosphite, tris(nonylphenyl) phosphite, tris(mono- and di-nonylphenyl) phosphite, 4,4'-butylidenebis(3-methyl-6-t-butylphenyl)-ditridecyl phosphite, distearylpentaerythritol diphosphite, and trilauryl trithiophosphite. The phenolic antioxidants and the phosphorus type antioxidants are preferred. The antioxidant is usually added in an amount of 0.01 to 20 parts, preferably 0.5 to 10 parts, by weight per 100 parts by weight of the binder resin of the layer to which it is incorporated. When the antioxidant is used in excess, the antioxidant may sometimes be oxidized when irradiated with intense light rays, which induces a chain oxidation reaction of the squarylium dye, resulting in deterioration of light resistance of the dye. In such cases, it is recommended to use a UV absorber in combination.

Examples of the UV absorbers include organic ones, such as benzotriazole compounds, e.g., 2-(2'-hydroxy-5'-methylphenyl)benzotriazole, 2-(2'-hydroxy-5'-butylphenyl) benzotriazole, 2-(2'-hydroxy-5'-t-butylphenyl) benzotriazole, 2-(2'-hydroxy-5'-t-octylphenyl)benzotriazole, 2-(2'-hydroxy-3',5'-di-t-butylphenyl)benzotriazole, 2-(2'-hydroxy-3',5'-di-t-amylphenyl)benzotriazole, 2-(2'-hydroxy-3'-t-butyl-5'-methylphenyl)-5-chlorobenzotriazole, and 2-(2'-hydroxy-3',5'-di-t-butylphenyl)-5-chlorobenzotriazole; benzophenone compounds, e.g., 2,4-dihydroxybenzophenone, 2-hydroxy-4- methoxybenzophenone, 2-hydroxy-4-octyloxybenzophenone, 2-hydroxy-4-dodecyloxybenzophenone, 2,2'-dihydroxy-4-methoxybenzophenone, and 2,2'-dihydroxy-4,4'-dimethoxybenzophenone; salicylates, e.g., phenyl salicylate, 4-t-butylphenyl salicylate, and 4-octylphenyl salicylate; and benzoates, e.g., 2,4-di-t-butylphenyl 3',5'-di-t-butyl-4'-hydroxybenzoate and hexadecyl 2,5-di-t-butyl-4-hydroxybenzoate; and inorganic ones, such as titanium dioxide, zinc oxide, cerium oxide, iron oxide, and barium sulfate.

Among these UV absorbers, preferred are those having a transmission of 50% at a wavelength between 350 nm and 420 nm, particularly between 360 nm and 400 nm. If the 50% transmission wavelength is shorter than 350 nm, the UV shielding power is weak. If it is longer than 420 nm, the UV absorber is unfavorably colored.

A commercially available UV cut filter may be utilized as a UV absorber-containing layer. Useful commercial UV cut filters include Sharp Cut Filter SC series (SC-38, SC-39 and SC-40) available from Fuji Photo Film Co., Ltd. and Acryprene available from Mitubishi Rayon Co., Ltd.

If desired, the display filter of the invention can contain other additives commonly employed in resin moldings, such as antistatic agents, lubricants, parting agents, flame retardants, flame retardant aids, and fillers, provided that the effects of the invention are not impaired.

The display filter of the invention, especially the one for PDPs can have additional layers, such as a near-infrared (IR) absorbing layer, an electromagnetic shielding layer, a antireflection layer, a non-glare layer, and an antiscratch resistant layer, and the like. These layers may be provided in an arbitrary order but preferably in the order described. The thickness of each of these layers is usually about 0.1 to 30 $\mu$m, preferably about 0.5 to 10 $\mu$m, each.

The near-IR absorbing layer is provided for the purpose of preventing near-IR emission from a PDP from interfering with remote control devices or optical communication systems. The near-IR absorbing layer can be provided as an independent resin layer containing a near-IR absorber by using the above-described binder resin, or it can be incorporated into any of an adhesive layer used for joining filter-constituent layers, which will be described later, an antiscratch resistant layer, an anchor coat which is provided when necessary, and a like layer. The near-IR absorber to be used is chosen arbitrarily from those capable of absorbing light in the region of 800 to 1000 nm in which remote control devices and optical communications systems operate typically. Those having a near-IR transmission of 10% or less in this region are preferred.

Examples of the near-IR absorbers include organic substances such as nitroso compounds and metal complexes thereof, cyanine compounds, thiol nickel complexes, dithiol nickel complexes, aminothiol nickel complexes, phthalocyanine compounds, naphthalocyanine compounds, triallylmethane compounds, immonium compounds, diimmonium compounds, naphthoquinone compounds, anthraquinone compounds, amino compounds, ammonium salt compounds, methine compounds, and squarylium compounds other than those according to the invention; and inorganic substances such as carbon black, indium tin oxide (ITO), antimony tin oxide, and oxides, carbonates or borides of metals belonging to the groups 4, 5 to 6 of the Periodic Table according to the IUPAC notation (1990). These near-IR absorbers can be used either individually or as a combination of two or more thereof.

The electromagnetic shielding layer is for preventing adverse influences of electromagnetic waves accompanying light emission from displays upon human bodies and electronic equipment. The electromagnetic shielding layer comprises a thin film of a metal or a metal oxide, such as silver, copper, indium oxide, zinc oxide, ITO, and antimony tin oxide, that can be formed by a known dry thin film formation technique such as vacuum evaporation, ion plating, sputtering, CVD or plasma enhanced CVD. A thin film of ITO is the most common electromagnetic shielding layer. A mesh-like perforated copper thin film and a laminate having alternating dielectric layers and metal layers are also suitable. The dielectric layers comprise a transparent metal oxide, e.g., indium oxide and zinc oxide, etc., and the metal layers generally comprise silver or a silver-palladium alloy. The laminate usually has an odd number (three to about thirteen) of layers with a dielectric layer being the first to be formed.

The electromagnetic shielding layer can be provided directly on any layer constituting the filter, or it can be formed on a separate resin film or a glass substrate by vacuum evaporation or sputtering and then joined with the filter.

The antireflection layer is provided to suppress surface reflection to prevent reflection of external light such as fluorescent lighting on the display surface. The antireflection layer includes a thin film of an inorganic material, such as a metal oxide, a fluoride, a silicide, a boride, a carbide, a nitride or a sulfide; a single layer of a resin, such as an acrylic resin or a fluorine-containing resin; and a multiple layer structure composed of such resins having different refractive indices. The inorganic thin film, which may have a single layer structure or a multi-layer structure, is formed directly on the display filter by the above-described dry thin film formation techniques or formed on a separate resin film or a glass substrate by vacuum evaporation or sputtering and then joined with the filter. The antireflection resin film is formed by a usual method of preparing a resin laminate, for example, by adhering a film or a sheet of an acrylic resin, a fluorine-containing resin, etc. to the display filter with an adhesive. The antireflection layer can also be provided by adhering a film having been subjected to antireflective surface treatment to the filter.

The non-glare layer is provided for the purpose of scattering transmitted light to broaden the viewing angle of the filter. It is formed by applying a dispersion of fine powder of silica, a melamine resin, an acrylic resin, etc. to any layer of the filter, followed by heat-curing or photo-curing, or adhering a film having been subjected to a non-glare treatment onto the filter.

The antiscratch resistance layer is formed by applying a solution or a dispersion of an acrylate (e.g., urethane acrylate, epoxy acrylate or polyfunctional acrylate) and a photopolymerization initiator in an organic solvent on any layer of the filter, preferably as a top layer of the filter, by a known coating technique, drying and photo-curing the coating layer.

The display filter according to the invention typically has a laminate structure which is basically composed of the above-mentioned transparent substrate and the dipyrazolylsquarylium compound-containing resin layer and, according to necessity, other layers such as the antioxidant-containing layer, the UV absorber-containing layer, the near-IR absorbing layer, the electromagnetic shielding layer, the antireflection layer, the non-glare layer, and the antiscratch resistance layer. The order and the method of building up these layers are not particularly limited. The laminate is generally prepared by joining the constituent layers with a pressure-sensitive adhesive with, if necessary, a transparent substrate being interposed between the layers. Adhesive properties and uniformity of the adhesive application can be improved by subjecting the adherend layer to a surface treatment, such as a corona discharge treatment, a glow discharge treatment, a plasma treatment, a flame treatment or a chemical treatment, or by coating the adherent layer with a known anchoring agent, such as isocyanate compounds, polyesters, polyethylene-imine, polybutadiene, and alkyl titanates.

The display filter can have a pressure-sensitive adhesive layer as an outermost layer on its back side with which to be adhered to a display device. The filter with a pressure-sensitive adhesive layer on its back is ready to be stuck to the front face of a display device either on or off the production line. Where the filter with an adhesive on its back has a near-IR absorbing layer, an electromagnetic shielding layer, etc. as described above, the need to separately set a near-IR absorbing filter, an electromagnetic shielding filter, etc. in sequence in front of a display device is eliminated simply by sticking the filter to the display device, thereby making the display assembly line simpler. Besides, the filter being integral with the display unit, the depth of the display device can be reduced.

The pressure-sensitive adhesive includes rubber adhesives, such as styrene-butadiene rubber, polyisoprene rubber, polyisobutylene rubber, natural rubber, neoprene rubber, chloroprene rubber, and butyl rubber, and low polymers of alkyl acrylates, such as methyl acrylate, ethyl acrylate and butyl acrylate. These adhesives can be used either alone or in combination with a tackifier, such as Piccolite, Polyvale or a rosin ester.

In case there is a fear that the surface of a display device heats up to cause gas to be evolved from the adhesive layer, a gas absorber, etc. would have to be incorporated into the adhesive layer. A preferred pressure-sensitive adhesive is such that exhibits a 180° peel strength of 300 g/cm or higher, particularly 400 g/cm or higher, when applied to a 3 mm thick glass sheet to form a 30 μm thick pressure-sensitive adhesive layer, to which a 30 μm thick polyester film is adhered, and allowed to stand at 80° C. for 10 hours.

The pressure-sensitive adhesive is applied as dissolved or dispersed in a solvent or a mixed solvent with a controlled viscosity by known coating techniques such as dip coating, flow coating, spraying, bar coating, gravure coating, roll coating, blade coating, and air knife coating, and dried to remove the solvent to form an adhesive layer. The solvents include halogen-containing solvents, alcohols, ketones, esters, ethers, aliphatic hydrocarbons and aromatic hydrocarbons.

The pressure-sensitive adhesive layer usually has a thickness of 5 to 100 μm, preferably 10 to 50 μm. The pressure-sensitive adhesive layer can be protected against dust adhesion with a release film until use. Where a release film is provided, a corner of the layer on which the pressure-sensitive adhesive layer is provided can be freed of the adhesive, or a non-adhesive film can be inserted at the corner between the layer and the adhesive layer, so that the release film may be stripped off with ease from that corner.

Care should be taken in sticking the filter to the front side of a display device not to entrap air bubbles, which would distort the image or make the image invisible.

The filter can previously be adhered to a transparent glass or resin sheet, which is then stuck to the front face of a display device.

The display devices to which the filter of the invention is applicable are known color displays that need color correction with a band pass filter, such as CRTs, vacuum fluorescent tubes, field-emission displays, PDPs, liquid crystal displays, and electroluminescence displays. The filter of the invention is particularly effective on known or commercial PDPs.

A PDP is a full color display device based on the following image formation principle. Pairs of display electrodes and cells are formed between a front glass substrate and a rear glass substrate. A rare gas (e.g., xenon or neon) is sealed in each cell, and the back wall of each cell (the front side of the rear glass substrate) is coated with a phosphor corresponding to each pixel, R, G and B. The rare gas in a cell is excited by a discharge between a pair of the display electrodes to produce ultraviolet light, with which the phosphor emits visible light corresponding to each pixel. Address electrodes are arrayed on the rear glass substrate. Signals are imposed to the address electrodes to select which discharge cells are to be displayed.

The present invention will now be illustrated in greater detail with reference to Examples, but it should be understood that the present invention is not construed as being limited thereto. Unless otherwise noted, all the percents and ratios are given by weight.

EXAMPLE 1

Synthesis of Compound No. 1 (see Table 1) ($R_4$=$R_5$=methyl, X=O):

In a reactor equipped with a Dean-Stark apparatus were put 0.39 g of 1,3-dimethyl-5-pyrazolone, 0.2 g of 3,4-dihydroxy-4-cyclobutene-1,2-dione, 25 ml of toluene, and 25 ml of n-butanol and heated under reflux for 4 hours. After completion of the reaction, the reaction mixture was allowed to cool. The precipitate was collected by filtration, washed with toluene and dried to give 0.43 g of the title compound.
Visible light absorption $\lambda_{max}$: 492 nm (in tetrahydrofuran)
MALDI-TOF mass spectrum: m/z=303 (M+H)

EXAMPLE 2

Synthesis of Compound No. 3 (see Table 1) ($R_4$=methyl, $R_5$=n-propyl, X=O):

The same process of Example 1 was followed, except for replacing 0.39 g of 1,3-dimethyl-5-pyrazolone with an equimole (0.49 g) of 1-methyl-3-n-propyl-2-pyrazolin-5-one, to give 0.53 g of the title compound.
Visible light absorption $\lambda_{max}$: 494 nm (in tetrahydrofuran)
MALDI-TOF mass spectrum: m/z=359 (M+H)

EXAMPLE 3

Synthesis of Compound No. 5 (see Table 1) ($R_4$=methyl, $R_5$=t-butyl, X=O):

The same process of Example 1 was followed, except for replacing 0.39 g of 1,3-dimethyl-5-pyrazolone with an equimole (0.54 g) of 3-t-butyl-1-methyl-2-pyrazolin-5-one to give 0.58 g of the title compound.
Visible light absorption $\lambda_{max}$: 502 nm (in tetrahydrofuran)
MALDI-TOF mass spectrum: m/z=387 (M+H)

EXAMPLE 4

Synthesis of Compound No. 17 (see Table 1) ($R_4$=methyl, $R_5$=phenyl, X=O):

The same process of Example 1 was followed, except for replacing 0.39 g of 1,3-dimethyl-5-pyrazolone with an equimole (0.61 g) of 3-phenyl-1-methyl-2-pyrazolin-5-one to give 0.43 g of the title compound.
Visible light absorption $\lambda_{max}$: 508 nm (in tetrahydrofuran)
MALDI-TOF mass spectrum: m/z=426 (M+H)

EXAMPLE 5

1) A mixed solution consisting of 0.24 g of a 0.25% solution of compound No. 3 synthesized in Example 2 in a 1/1 mixture of dimethoxyethane (DME) and toluene and 1.0 g of a 20% DME solution of an acrylic resin BR-83, available from Mitubishi Rayon Co., Ltd., was applied on a 100 μm thick polyethylene terephthalate film (T100E, available from Mitubishi Polyester Film Corp.) with a bar coater and dried to prepare a filter having a 6 μm thick coating film.

The transmission of the coating film was measured with a spectrophotometer U-3500 supplied by Hitachi, Ltd. (hereinafter the same). The resulting transmission spectrum is shown in FIG. 1. The minimum transmission was 35.26% at a wavelength of 494 nm, and the half-value width at the minimum was 44.1 nm. There was no other minimum than that of 494 nm, proving that the filter exhibits satisfactory visible light transmission.

2) The filter was placed in a thermostat set at 100° C. for 100 hours. The dye retention (%) was determined from the absorbance as measured with the Hitachi spectrophotometer U-3500. As a result, the dye retention was 100% with no deterioration, indicating very high heat resistance of compound No. 3.

EXAMPLE 6

Figure 2:
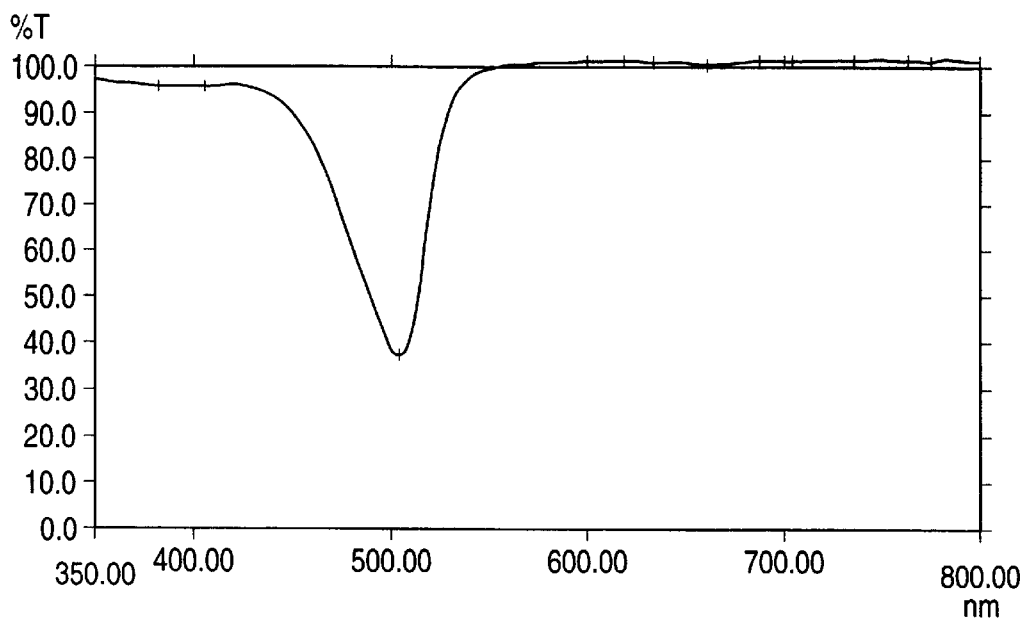
FIG. 2 is a transmission spectrum of the coating film obtained in Example 6.

A filter was prepared in the same manner as in Example 5, except for replacing the compound No. 3 solution with 0.24 g of a 0.25% solution of compound No. 5 synthesized in Example 3 in a 1/1 mixed solvent of DME and toluene. The transmission spectrum of the coating film is shown in FIG. 2. The coating film showed a minimum transmission of 36.52% at a wavelength of 503 nm with a half-value width of 46.9 nm. There was no other minimum than that at 503 nm, proving that the filter exhibits satisfactory transmission.

2) The filter was placed in a thermostat set at 100° C. for 100 hours. The dye retention (%) was determined from the absorbance as measured with the Hitachi spectrophotometer U-3500. As a result, the dye retention was 100% with no deterioration, indicating very high heat resistance of compound No. 5.

EXAMPLE 7

Figure 3:
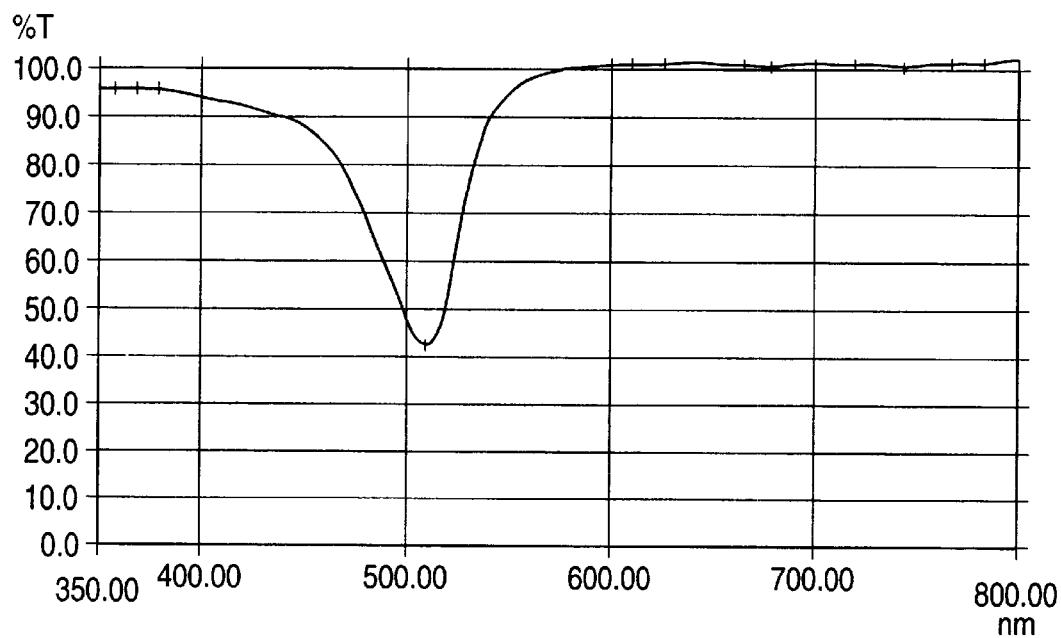
FIG. 3 is a transmission spectrum of the coating film obtained in Example 7.

A filter having a 5 μm thick coating film was prepared in the same manner as in Example 5, except for replacing the compound No. 3 solution with 0.24 g of a 0.38% solution of compound No. 17 synthesized in Example 4 in a 1/1 mixed solvent of DME and toluene and replacing the 20% DME solution of the acrylic acid BR-83 with 1.0 g of a 18% DME solution of an acrylic resin BR-80 from Mitubishi Rayon Co., Ltd. The transmission spectrum of the coating film is shown in FIG. 3. The coating film showed a minimum transmission of 42.23% at a wavelength of 508 nm with a half-value width of 50.6 nm. There was no other minimum than that at 508 nm, proving that the filter exhibits satisfactory transmission. As a result of the same heat resistance test as in Example 5, compound No. 17 was proved excellent in heat resistance, showing a retention of 99.6%.

2) The filter was placed in a thermostat set at 100° C. for 100 hours. The dye retention (%) was determined from the absorbance as measured with the Hitachi spectrophotometer U-3500. As a result, the dye retention was 99.6% with no deterioration, indicating very high heat resistance of compound No. 17.

EXAMPLE 8

In 1.59 g of a 3/1 mixed solvent of DME and toluene were dissolved 2.0 mg of compound No. 3 synthesized in Example 2 and 5.0 mg of a diphenylsquarylium dye of formula (III-1) which is for neon luminescence cutting for a PDP. A 0.12 g portion of the dye solution was mixed with 1.0 g of a 20% DME solution of a polyester resin Vylon 200, available from Toyobo Co., Ltd., to prepare a coating composition. The coating composition was applied to the same substrate as used in Example 5 and dried to form a 6 μm thick coating film.

Figure 4:
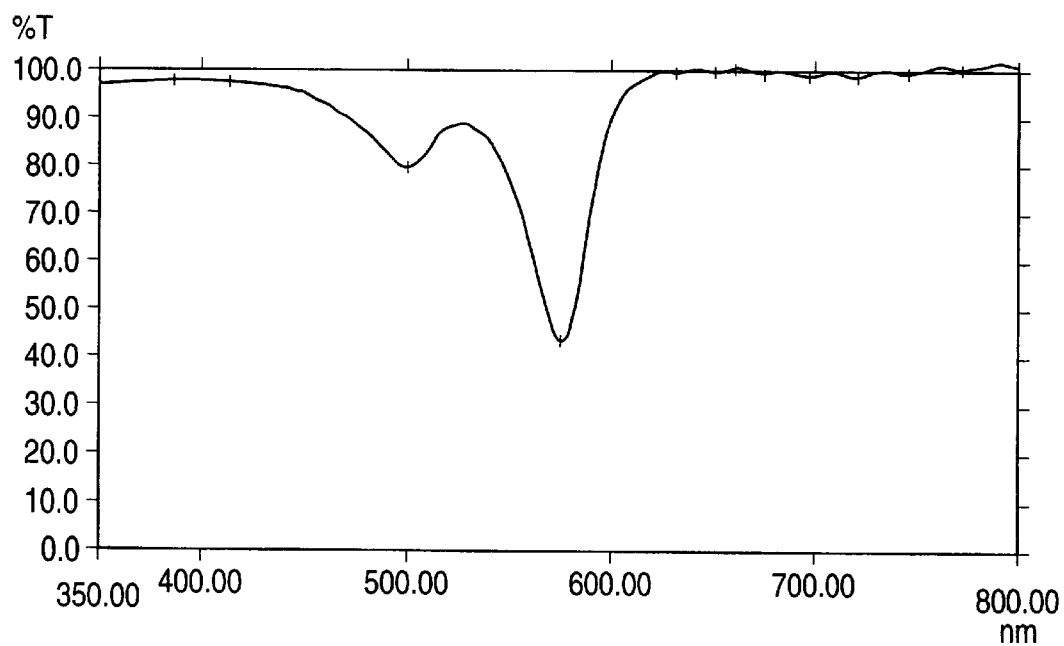
FIG. 4 is a transmission spectrum of the coating film obtained in Example 8.

The transmission spectrum of the coating film measured by Hitachi spectrophotometer U-3500 is shown in FIG. 4. The coating film showed a minimum transmission of 43.35% at a wavelength of 576 nm and of 79.29% at 500 nm. The filter was very bright, having a visible light transmission of 77.87%. According to the CIE L*a*b* chromaticity diagram (2° field; CIE standard source C), the color of the filter was L*=90.46, a*=10.07, and b*=−11.58, which indicates a shift to red from the color of a filter prepared in the same manner except for using only the compound (III-1) (L*=91.27, a*=8.00, b*=−11.30).

EXAMPLE 9

A filter for a PDP was prepared in the same manner as in Example 5, except for replacing the 20% DME solution of acrylic resin BR-83 with 1.0 g of a 18% DME solution of an acrylic resin BR-80 available from Mitubishi Rayon. A UV-cut filter (Sharp Cut Filter SC-39, available from Fuji Photo Film) was superposed on the squarylium compound-containing resin layer to obtain a light-resistant filter for a PDP.

The UV-cut filter side of the filter was exposed to light using a xenon fadeometer (FAL-25AX-HC.B.EC, available from Suga Test Instruments) for 80 hours. As a result, the dye retention (%) was 90.0%, proving satisfactory light resistance of the filter. When the filter without the UV-cut filter was subjected to the same light resistance test, the dye retention was 79.5%.

EXAMPLE 10

A filter for a PDP was prepared in the same manner as in Example 6, except for replacing the 20% DME solution of acrylic resin BR-83 with 1.0 g of a 18% DME solution of an acrylic resin BR-80 available from Mitubishi Rayon. A UV-cut filter (Sharp Cut Filter SC-39, available from Fuji Photo Film) was superposed on the squarylium compound-containing resin layer to obtain a light-resistant filter for a PDP.

The UV-cut filter side of the filter was exposed to light using a xenon fadeometer (FAL-25AX-HC.B.EC, available from Suga Test Instruments) for 80 hours. As a result, the dye retention (%) of the filter was 96.8%, proving excellent light resistance of the filter. When the filter without the UV-cut filter was subjected to the same light resistance test, the dye retention was 91.1%.

EXAMPLE 11

A UV-cut filter (Sharp Cut Filter SC-39, available from Fuji Photo Film) was superposed on the squarylium compound-containing resin layer of the filter obtained in Example 7 to prepare a light-resistant filter for a PDP.

The UV-cut filter side of the filter was exposed to light using a xenon fadeometer (FAL-25AX-EC.B.EC, available from Suga Test Instruments) for 80 hours. As a result, the dye retention (%) of the filter was 94.9%, proving excellent light resistance of the filter. When the filter without the UV-cut filter was subjected to the same light resistance test, the dye retention was 85.4%.

While the invention has been described in detail and with reference to specific examples thereof, it will be apparent to one skilled in the art that various changes and modifications can be made therein without departing from the spirit and scope thereof.

This application is based on Japanese patent applications No. 2000-149260 filed on May 22, 2000 and No. 2000-218194 filed on Jul. 19, 2000, the entire contents thereof being hereby incorporated by reference.

What is claimed is:

1. In a process for making a filter of a display device, wherein said filter contains coloring matter, the improvement which comprises using coloring matter comprising a dipyrazolylsquarylium compound represented by formula (I):

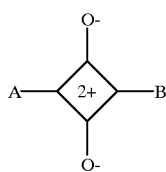

wherein A and B each independently represent a substituted or unsubstituted pyrazolyl group.

2. The process according to claim 1, wherein said dipyrazolyisquarylium compound is represented by formula (II):

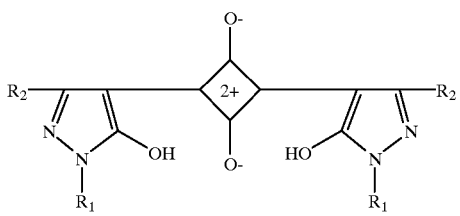

wherein $R_1$ represents a substituted or unsubstituted alkyl group; $R_2$ represents a substituted or unsubstituted alkyl group or a substituted or unsubstituted aryl group; and $R_1$ and $R_2$ may be the same or different.

3. The process according to claim 2, wherein $R_2$ is a substituted or unsubstituted alkyl group.

4. A filter for a display device, which comprises a substrate having thereon at least a layer containing coloring matter comprising a dipyrazolyisquarylium compound represented by formula (I):

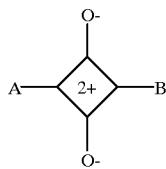

wherein A and B each independently represent a substituted or unsubstituted pyrazolyl group.

5. The filter for a display device according to claim 4, which further has a layer containing an ultraviolet absorber at a position farther from the side to be stuck to the display device than said layer containing the coloring matter.

6. A plasma display panel containing the filter according to claim 4.

7. The plasma display panel according to claim 6, which further comprises a diphenylsquarylium compound represented by formula (III):

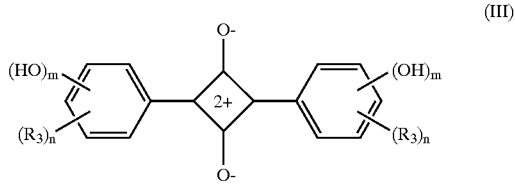

wherein $R_3$ represents a halogen atom, a substituted or unsubstituted alkyl group, a substituted or unsubstituted alkoxy group or a substituted or unsubstituted alkenyl group; m represents an integer of 1 to 4; and n represents an integer of 0 to 4, in said layer containing said coloring matter or in a layer independent of said layer containing said coloring matter.

8. The filter for a display device according to claim 4, wherein said dipyrazolylsquarylium compound is represented by formula (II):

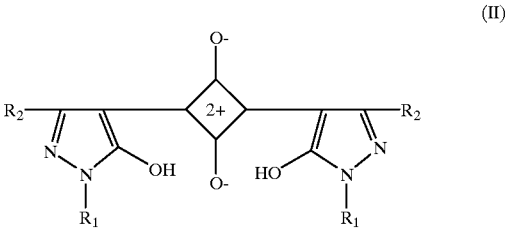

wherein $R_1$ represents a substituted or unsubstituted alkyl group; $R_2$ represents a substituted or unsubstituted alkyl group or a substituted or unsubstituted aryl group; and $R_1$ and $R_2$ may be the same or different.

9. The filter for a display device according to claim 4, wherein the dipyrazolylsquarylium compound has a minimum transmission in a wavelength region of from 480 to 520 nm.

10. The filter for a display device according to claim 4, wherein A and B each independently is represented by formula (IV):

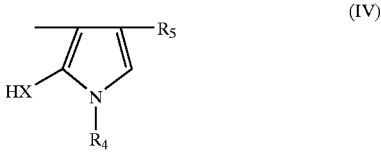

wherein $R_4$ represents a substituted or unsubstituted alkyl group or a substituted or unsubstituted aryl group; $R_5$ represents a substituted or unsubstituted alkyl group, a substituted or unsubstituted alkoxy group, a substituted or unsubstituted aryl group, a substituted or unsubstituted amino group, a substituted or unsubstituted alkoxycarbonyl group or a substituted or unsubstituted aryloxycarbonyl group; and X represents an oxygen atom or an NH group.

11. The filter for a display device according to claim 4, wherein A and B are the same.

12. A process of making the filter according to claim 4, which comprises forming a laminate of said substrate and said at least a layer containing coloring matter, which layer contains a binder resin.

13. A squarylium compound represented by formula (II):

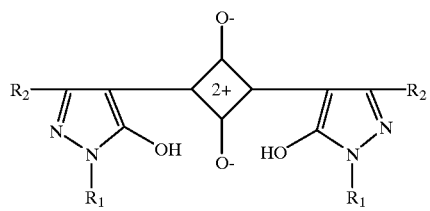

wherein $R_1$ represents a substituted or unsubstituted alkyl group; $R_2$ represents a substituted or unsubstituted alkyl group or a substituted or unsubstituted aryl group; and $R_1$ and $R_2$ may be the same or different.

14. The squarylium compound according to claim 13, wherein $R_2$ is a substituted or unsubstituted alkyl group.

15. A process for synthesizing the squarylium compound according to claim 13, comprising carrying out a dehydrating condensation between 1 mol of squarylic acid and 2 mol of a pyrazolyl compound represented by formula (VI):

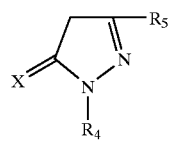

* * * * *